United States Patent
Linguraru et al.

(10) Patent No.: US 11,880,980 B2
(45) Date of Patent: Jan. 23, 2024

(54) MEDICAL ANATOMY QUANTIFICATION: COMPUTER-AIDED DIAGNOSIS TOOL

(71) Applicant: CHILDREN'S NATIONAL MEDICAL CENTER, Washington, DC (US)

(72) Inventors: Marius George Linguraru, Washington, DC (US); Juan Jose Cerrolaza, Washington, DC (US); Craig Andrew Peters, Dallas, TX (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 868 days.

(21) Appl. No.: 16/309,825

(22) PCT Filed: Jun. 19, 2017

(86) PCT No.: PCT/US2017/038149
§ 371 (c)(1),
(2) Date: Dec. 13, 2018

(87) PCT Pub. No.: WO2017/219024
PCT Pub. Date: Dec. 21, 2017

(65) Prior Publication Data
US 2019/0311805 A1    Oct. 10, 2019

Related U.S. Application Data

(60) Provisional application No. 62/351,859, filed on Jun. 17, 2016.

(51) Int. Cl.
*G06T 7/12* (2017.01)
*G06T 7/13* (2017.01)
(Continued)

(52) U.S. Cl.
CPC .............. *G06T 7/12* (2017.01); *A61B 5/201* (2013.01); *A61B 5/7267* (2013.01);
(Continued)

(58) Field of Classification Search
CPC ...................................................... G16H 50/20
See application file for complete search history.

(56) References Cited

U.S. PATENT DOCUMENTS

2003/0007598 A1 *  1/2003  Wang ..................... A61B 6/463
                                                        378/37
2007/0167699 A1 *  7/2007  Lathuiliere ............. G06T 7/149
                                                        600/407
(Continued)

OTHER PUBLICATIONS

International Search Report and Written Opinion dated Oct. 20, 2017 in PCT/US2017/038149 filed on Jun. 19, 2017.
(Continued)

*Primary Examiner* — Oneal R Mistry
(74) *Attorney, Agent, or Firm* — Oblon, McClelland, Maier & Neustadt, L.L.P.

(57) ABSTRACT

Described is a method for segmenting an anatomical part, including identifying a landmark on a contour/surface of a 2D/3D model of the anatomical part in an ultrasound image, assigning a weight to the landmark, identifying different appearance patterns of a region around the landmark based on a previously stored training set; and applying a filter to the different appearance patterns of the region around the landmark in order to identify contours of the anatomical part.

26 Claims, 6 Drawing Sheets

(51) Int. Cl.
G06T 7/155 (2017.01)
G16H 50/20 (2018.01)
G16H 30/40 (2018.01)
A61B 5/20 (2006.01)
A61B 5/00 (2006.01)
G06T 7/00 (2017.01)
G06T 7/40 (2017.01)
G06T 7/149 (2017.01)
G06F 18/214 (2023.01)
G06F 18/231 (2023.01)
G06F 18/2411 (2023.01)

(52) U.S. Cl.
CPC .......... *G06F 18/214* (2023.01); *G06F 18/231* (2023.01); *G06F 18/2411* (2023.01); *G06T 7/0012* (2013.01); *G06T 7/13* (2017.01); *G06T 7/149* (2017.01); *G06T 7/155* (2017.01); *G06T 7/40* (2013.01); *G16H 30/40* (2018.01); *G16H 50/20* (2018.01); *G06T 2207/10132* (2013.01); *G06T 2207/10136* (2013.01); *G06T 2207/20116* (2013.01); *G06T 2207/30084* (2013.01)

(56) References Cited

U.S. PATENT DOCUMENTS

2007/0238995 A1 10/2007 Sui et al.
2012/0182294 A1* 7/2012 Cordon Garcia ....... G06T 17/00
                                                    345/419
2014/0247977 A1* 9/2014 Han ...................... G06T 7/11
                                                    382/159
2015/0023575 A1* 1/2015 Valadez ................. G06T 7/11
                                                    382/131
2015/0148657 A1* 5/2015 Shashar ............... A61B 8/0875
                                                    600/440
2015/0173715 A1 6/2015 Raghavan et al.
2015/0201878 A1 7/2015 Chen et al.
2016/0063720 A1* 3/2016 Han ...................... G06T 7/10
                                                    382/131

OTHER PUBLICATIONS

Extended European Search Report dated Apr. 2, 2020, in Patent Application No. 17814260.0, 9 pages.
Cerrolaza, J. J. et al., "Segmentation of Kidney in 3D-Ultrasound Images using Gabor-based Appearance Models", IEEE, XP032779226, Apr. 29, 2014, pp. 633-636.
Cerrolaza, J. J. et al., "Renal Segmentation From 3D Ultrasound via Fuzzy Appearance Models and Patient-Specific Alpha Shapes", IEEE Journals & Magazine, XP055677676, May 24, 2016, 20 pages.

* cited by examiner

MEDICAL ANATOMY QUANTIFICATION: COMPUTER-AIDED DIAGNOSIS TOOL

CROSS REFERENCE TO RELATED APPLICATIONS

This application claims the benefit of priority of U.S. Patent Application No. 62/351,859, filed Jun. 17, 2016 the entire contents of all are incorporated herein by reference.

BACKGROUND

Technical Field

Among other things, the present disclosure is related to a computer aided approach for the automatic assessment of disease severity in patients.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Thanks to its non-ionizing nature, ultrasound (US) imaging is the preferred diagnostic modality for the evaluation of the kidney and the urinary track. However, there is a lack of correlation of ultrasound with renal function. In addition, the use of ultrasound as diagnostic tool is limited by the subjective visual interpretation of radiologists. As a result, the severity of a certain diseases such as hydronephrosis in children is evaluated by invasive and ionizing diuretic renograms.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

The present embodiments provide a unique approach for the segmentation of an anatomical part which can be used, in a non-limiting example, in the treatment of hydronephrosis without the need for invasive and ionizing diuretic renograms. This approach can also be used in many other medical contexts including the characterizations of portions of the anatomy.

Embodiments of the disclosed subject matter are directed to a method for segmenting an anatomical part, including identifying a landmark on a contour/surface of a 2D/3D model of the anatomical part in an ultrasound image, assigning a weight to the landmark, identifying different appearance patterns of a region around the landmark based on a previously stored training set; and applying a filter to the different appearance patterns of the region around the landmark in order to identify contours of the anatomical part.

Also described is a method for segmenting a portion of an anatomical part, including identifying echogenic regions of the anatomical part in an ultrasound image to differentiate the portion of the anatomical part from other portions of the anatomical part, generating, using the identified echogenic regions of the anatomical part, a positional map of the portion of the anatomical part, and incorporating patient-specific constraints to delimitate the portion of the anatomical part.

Embodiments also include a method for characterizing functionality of an anatomical part to identify severity of a medical condition, the method including delineating the anatomical part and segmenting a portion of the anatomical part in ultrasound images, extracting morphological features of the anatomical part and the portion of the anatomical part using image analysis, selecting an optimal subset of the morphological features using a supervised or an unsupervised feature selection framework, and classifying each feature in the optimal subset as critical or non-critical based on a threshold and a classifier, the classifier being one of linear discriminant analysis or a support vector machine.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

Reference throughout the specification to "one embodiment" or "an embodiment" means that a particular feature, structure, characteristic, operation, or function described in connection with an embodiment is included in at least one embodiment of the disclosed subject matter. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments. Further, it is intended that embodiments of the disclosed subject matter can and do cover modifications and variations of the described embodiments.

It must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the disclosed subject matter to any particular orientation or configuration. Furthermore, terms such as "first," "second," "third," etc., merely identify one of a number of portions, components, points of reference, operations and/or functions as described herein, and likewise do not necessarily limit embodiments of the disclosed subject matter to any particular configuration or orientation.

Figure 1:
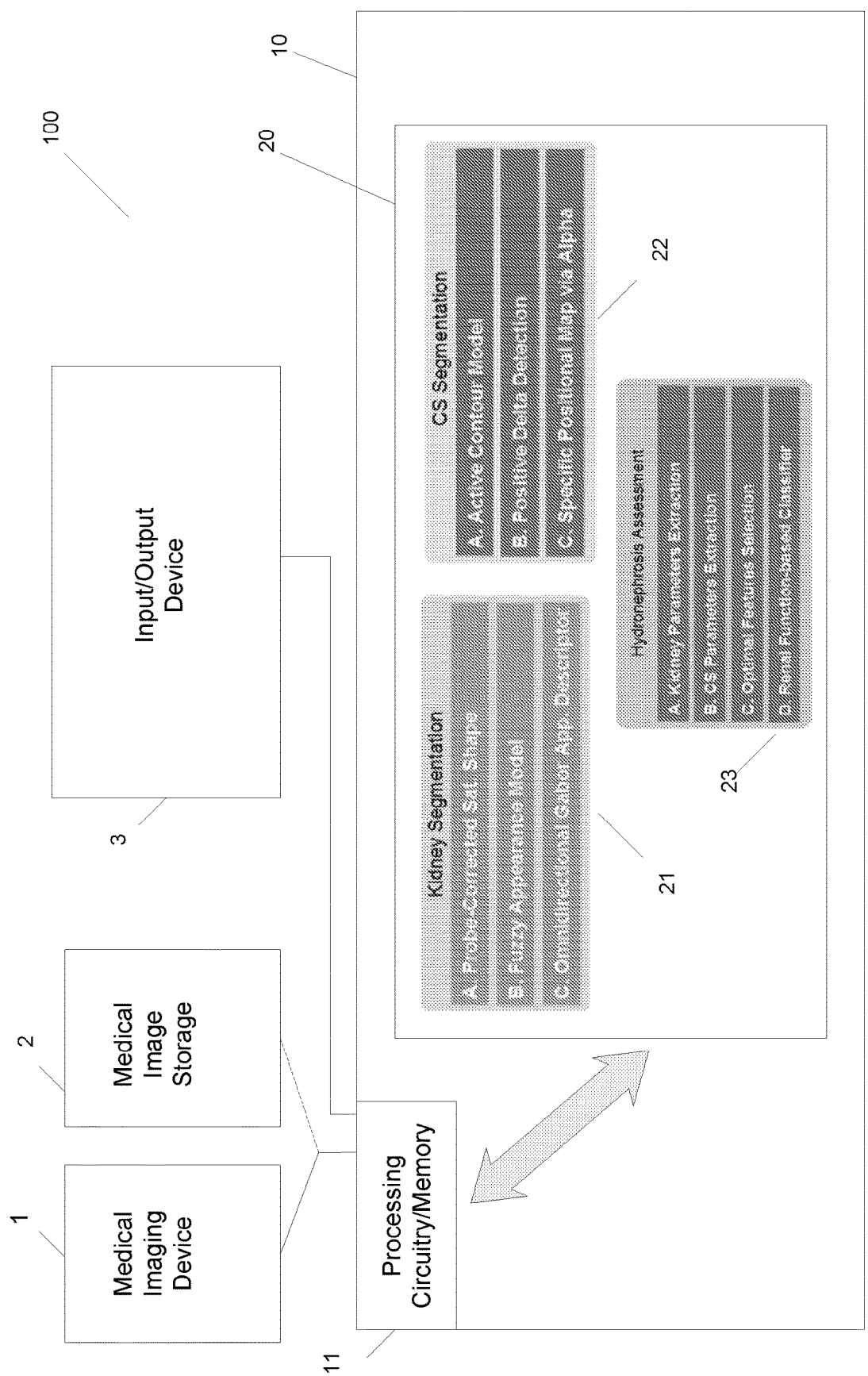
FIG. 1 illustrates a block diagram according to an embodiment of the present disclosure.

FIG. 1 depicts an exemplary overview of the segmentation and characterization system 100 (herein system 100) according to one or more aspects of the disclosed subject matter. The system 100 may include a medical imaging device (such as an ultrasound machine or any other type of imaging or medical imaging hardware), an input/output device 3 (such as a touch screen or a display device and a keyboard/mouse) and computing device 10 (which may or may not be incorporated into the medical imaging device). The computing device 10 includes processing circuitry/memory 11 (such as a CPU and RAM) and implements via the processing circuitry/memory 11 software 20 having a number of functions 21, 22 and 23. The first function 21 relates to segmentation of a whole (for example segmentation of an entire kidney or any other anatomical part). This function is described in the process shown in FIG. 2. The second function 22 relates to segmentation of a part (for example segmentation of a collecting system (CS) of a kidney or any other smaller portion of the whole of the anatomical part). This function is described in the process shown in FIG. 3. The third function 23 relates to characterizing functionality of an anatomical part (for example to identify severity of a medical condition such as hydronephrosis). This function is described in the process shown in FIG. 4.

Figure 2:
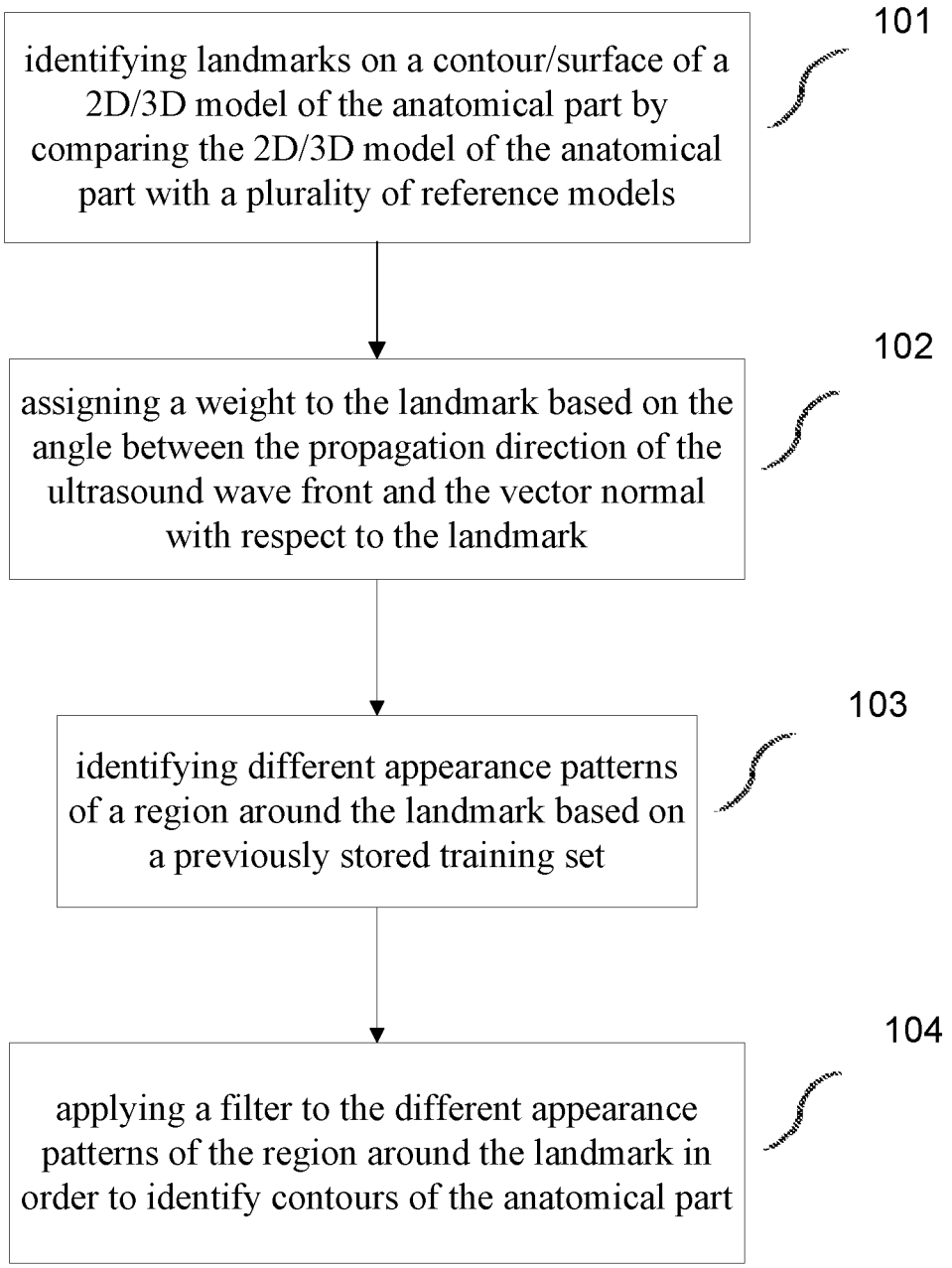
FIG. 2 illustrates a illustrates a flowchart describing segmentation of an anatomical part in 2D/3D ultrasound images.

FIG. 2 illustrates a flowchart describing segmentation of an anatomical part (for example, a kidney) in 2D/3D ultrasound images. In Step 101, landmarks on a contour/surface of a 2D/3D model of the anatomical part are identified by comparing the 2D/3D model of the anatomical part with a plurality of reference models. In Step 102, a weight to the landmark is assigned based on the angle between the propagation direction of the ultrasound wave front and the vector normal with respect to the landmark. Further, in Step 103, different appearance patterns of a region around the landmark are identified based on a previously stored training set. Finally, in Step 104, a filter is applied to the different appearance patterns of the region around the landmark in order to identify contours of the anatomical part.

Figure 3:
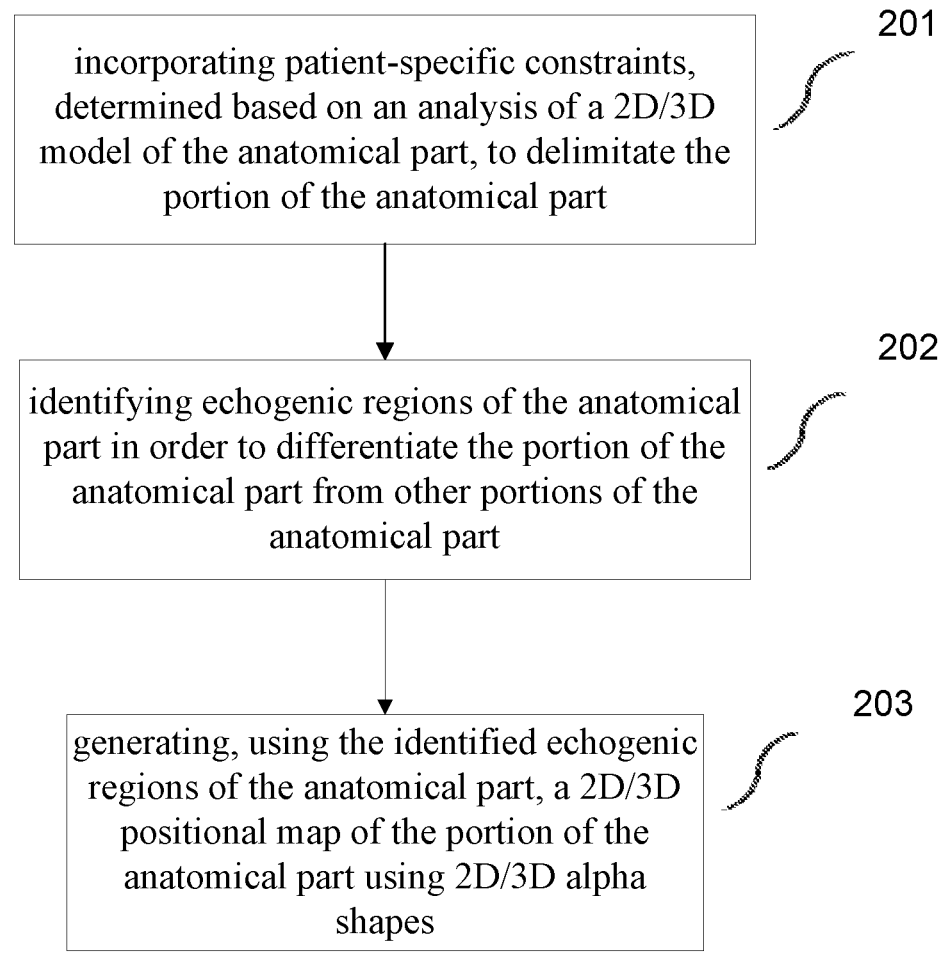
FIG. 3 illustrates a flowchart describing segmentation of a portion of an anatomical part.

FIG. 3 illustrates a flowchart describing segmentation of a portion of an anatomical part (for example, a collecting system). In Step 201, patient-specific constraints, determined based on an analysis of a 2D/3D model of the anatomical part, are incorporated to delimitate the portion of the anatomical part. The patient-specific constraint refers to the use of a particular positional map that was generated as additional constraint when segmenting the collecting system. The attached documents refer to patient-specific constraints because the positional map is computed specifically for each patient. The steps are: $1^{st}$—Identify echogenic regions within the kidney (typically, these echogenic regions represent renal fat that surround the collecting system), $2^{nd}$—Use the alpha shapes to identify the contour defined by those echogenic regions, and $3^{rd}$—The resulting region is used to define the positional map, which will be used as patient-specific constraints when segmenting the collecting system. Since the renal fat typically surrounds the collecting system, the obtained contour will define the region where it is more likely to find the collecting system, and thus, making it easier to segment it in ultrasound images. In Step 202, echogenic regions of the anatomical part are identified in order to differentiate the portion of the anatomical part from other portions of the anatomical part. Finally, in Step 203, a 2D/3D positional map of the portion of the anatomical part is generated using the identified echogenic regions of the anatomical part and using 2D/3D alpha shapes.

Figure 4:
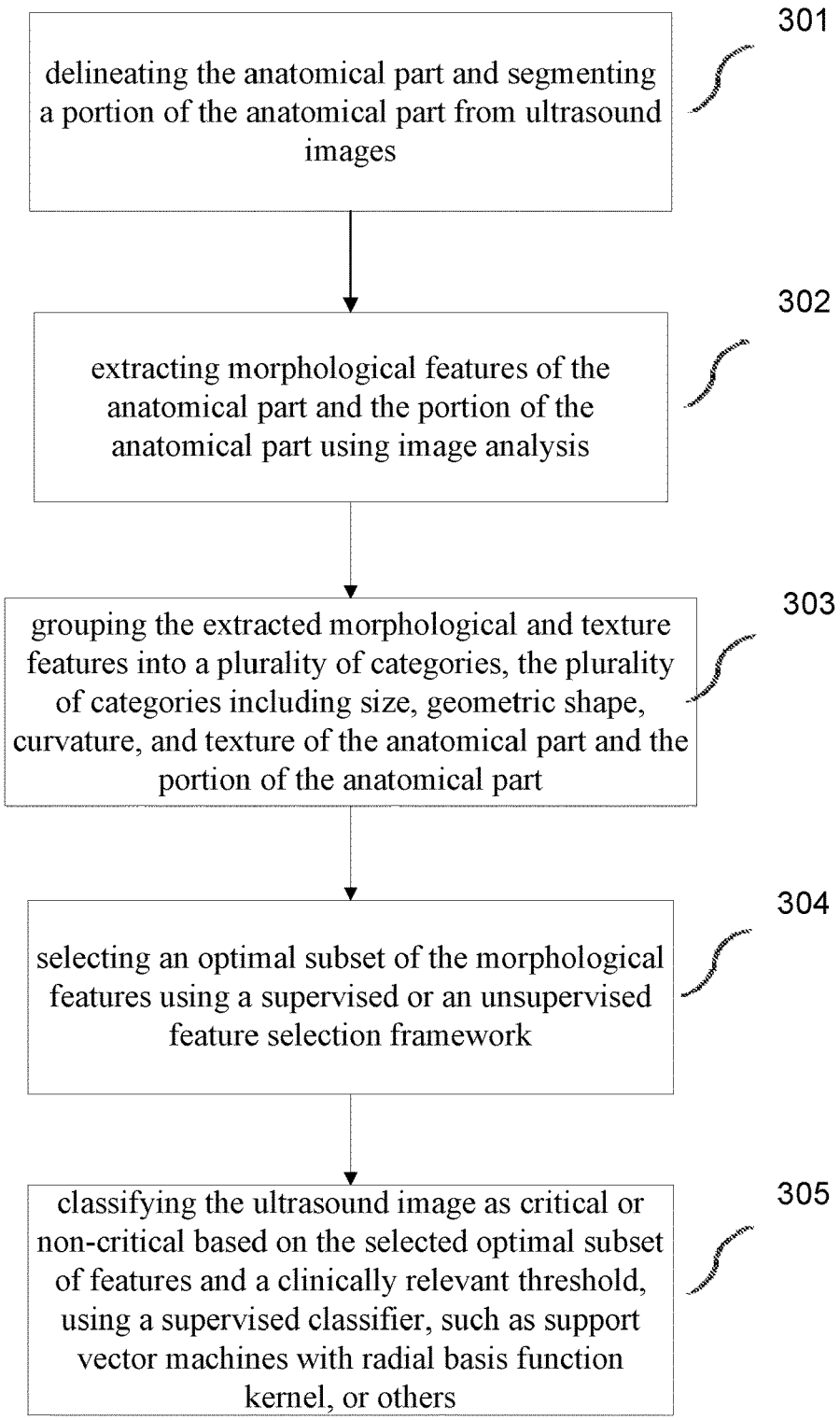
FIG. 4 illustrates a flowchart describing a method for characterizing functionality of an anatomical part to identify severity of a medical condition.

FIG. 4 illustrates a flowchart describing a method for characterizing functionality of an anatomical part to identify severity of a medical condition (for example, hydronephrosis). In Step 301, the anatomical part is delineated and a portion of the anatomical part is segmented from a 2D/3D ultrasound image. It should be noted that any known method to delineate the anatomical part and to segment the portion of the anatomical part may be used. Additionally, the segmentation processes described above with regard to Flowcharts 1 and 2 may also be used to delineate the anatomical part and to segment the portion of the anatomical part. In Step 302, morphological and texture features of the anatomical part and the portion of the anatomical part are extracted using image analysis. Further, in Step 303, the extracted morphological features are grouped into a plurality of categories, the plurality of categories including size, geometric shape, curvature, and texture of the anatomical part and the portion of the anatomical part. In Step 304, an optimal subset of the morphological features is selected using a supervised or an unsupervised feature selection framework. Finally, each feature in the optimal subset is classified as critical or non-critical based on a threshold and a classifier, e.g. linear discriminant analysis, support vector machine, or other. Further details of the method for characterizing functionality of an anatomical part to identify severity of a medical condition are described in the attached documents.

Figure 5:
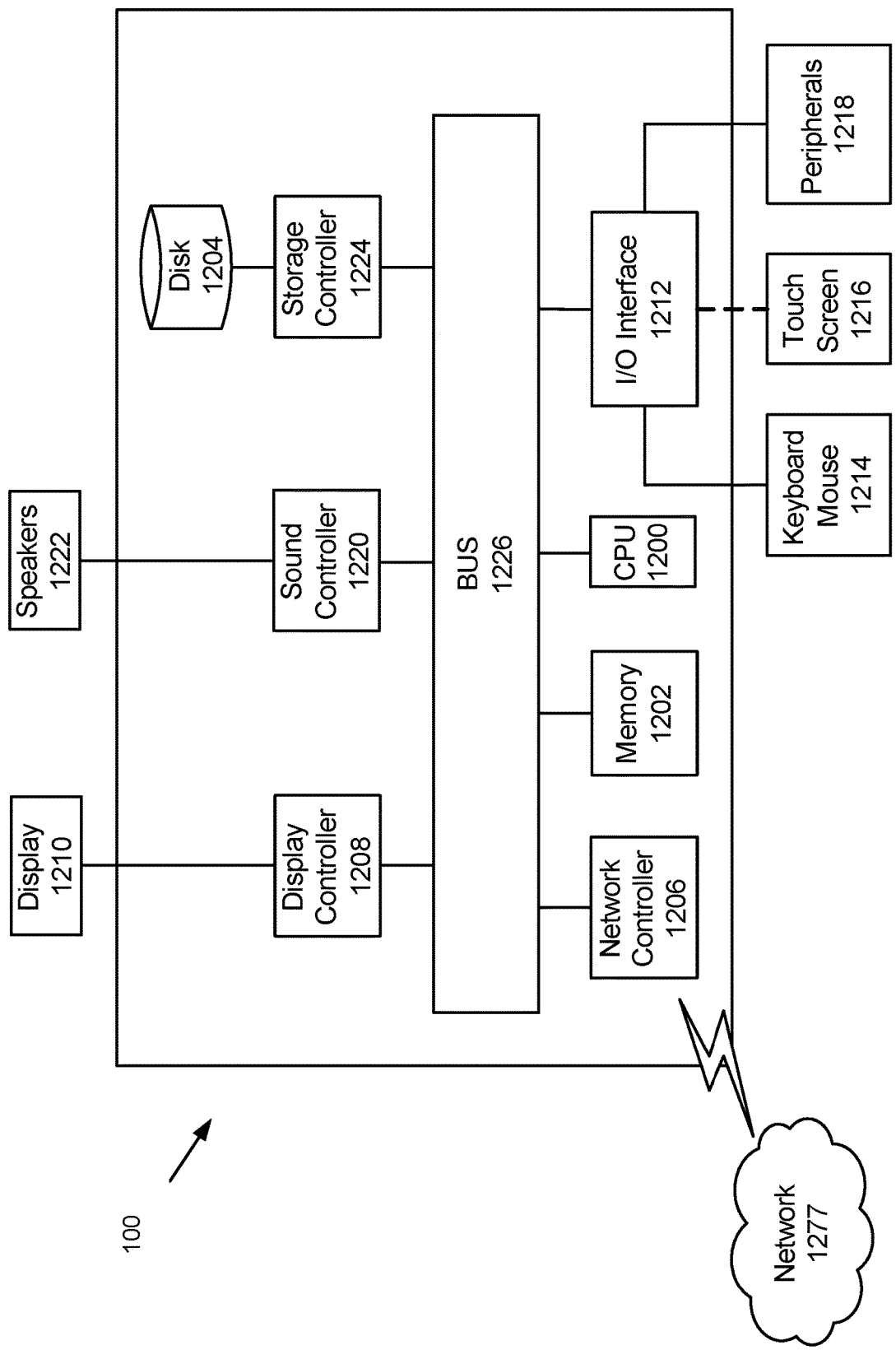
FIG. 5 illustrates a hardware description of a device according to exemplary implementations of the present disclosure.

The processes described above and described throughout the presently filed application can be performed on a device including circuitry or CPU. FIG. 5 illustrates a hardware description of a device 100 according to exemplary implementations of the present disclosure. The structure of the device 100 illustrated in the FIG. 5 is an exemplary computer system as mentioned herein. Although the specific description provided below regarding FIG. 5 pertains to a computer system, it should be appreciated that corresponding structures or components can be provided in the other devices discussed herein, and not all of the components or connections illustrated in the above figure may be provided in particular devices.

In FIG. 5, the device 100 includes a CPU 1200 which performs/executes the processes and algorithms described herein. Process data and instructions may be stored in memory 1202. Processes and instructions may also be stored on a storage medium disk 1204 such as a hard drive (HDD) or portable storage medium or may be stored remotely. Further, executable instructions are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device communicates, such as a server or computer.

Further, executable instructions may be provided as a utility application, background daemon, or component of an operating system, or combination thereof, executing in conjunction with CPU 1200 and an operating system such as Android, iOS, Windows Mobile, Windows Phone, Microsoft Windows 7 or 8, UNIX, Solaris, LINUX, Apple MAC-OS and other operating systems.

CPU 1200 may be a Xenon or Core processor from Intel of America or an Opteron processor from AMD of America, especially in implementations where the device is a computer or a server. Other processors can be utilized when the device is, e.g., a mobile phone, a smartphone, a tablet, a battery-operated device, or a portable computing device. For example, a Qualcomm Snapdragon or ARM-based processor can be utilized. The CPU 1200 may be implemented on an FPGA, ASIC, PLD or using discrete logic circuits, as one of ordinary skill in the art would recognize. Further, CPU 1200 may be implemented as multiple processors cooperatively working in parallel to perform the instructions of the processes described above, and the CPU 1200 may incorporate processing circuitry other than generic processing circuitry, whereby the CPU 1200 includes circuitry to execute specific display and user interface controls that may otherwise be provided for by other discrete circuitry.

The device in the above figure also includes a network controller 1206, such as an Intel Ethernet PRO network interface card from Intel Corporation of America, for interfacing with network 1277 when the device is a computer or a server, for example. When the device is a portable electronic device, the network controller 1206 includes a radio that may be incorporated into the CPU 1200. The radio may incorporate various wireless communication technologies as separate circuits or shared circuitry, and the technologies can incorporate LTE, GSM, CDMA, WiFi, Bluetooth, NFC, infrared, FM radio, AM radio, ultrasonic, and/or RFID circuitry. The network 1277 can be a public network, such as the Internet, or a private network such as an LAN or WAN network, or any combination thereof and can also include PSTN or ISDN sub-networks. The network 1277 can also be wired, such as an Ethernet network, or can be wireless such as a cellular network including EDGE, 3G and 4G wireless cellular systems. The network 1277 may be connected to server 1240 to retrieve a list of classroom registration and/or allow the device to download and install application software to implement aspects of this disclosure. The wireless network can also be WiFi, Bluetooth, or any other wireless form of communication. In the exemplary implementations discussed herein, the network 1277 can include both the Internet and a Bluetooth communication channel, but this is not limiting as other combinations are applicable when a different short-range communication technology is utilized.

The device further includes, when the device is a computer or a server, a display controller 1208, such as a NVIDIA GeForce GTX or Quadro graphics adaptor from NVIDIA Corporation of America for interfacing with display 1210, such as a Hewlett Packard HPL2445w LCD monitor. A general purpose I/O interface 1212 interfaces with a keyboard and/or mouse 1214 as well as a touch screen panel 1216 on or separate from display 1210. General purpose I/O interface also connects to a variety of peripherals 1218 including printers and scanners. When the device is, e.g., a smartphone, the display 1210 can be integrated into the device and can be a touchscreen display. Further, the display controller 1208 can be incorporated into the CPU 1200.

A sound controller 1220 is also provided in the device, such as Sound Blaster X-Fi Titanium from Creative, to interface with speakers/microphone 1222 thereby providing sounds and/or music. The sound controller 1220 can also be incorporated into the CPU 1200 when the device is, e.g., a smartphone.

The general purpose storage controller 1224 connects the storage medium disk 1204 with communication bus 1226, which may be an ISA, EISA, VESA, PCI, or similar, for interconnecting all or some of the components of the device. A description of the general features and functionality of the display 1210, keyboard and/or mouse 1214, as well as the display controller 1208, storage controller 1224, network controller 1206, sound controller 1220, and general purpose I/O interface 1212 is omitted herein for brevity.

One goal of the system is to quantify the shape of the kidney and its collecting system and allow the characterization of hydronephrosis severity from ultrasound images of the kidney. The invention may preclude the need to use more invasive diagnostic procedures such as diuretic renography on patients with hydronephrosis, and identify those cases that would benefit from surgery. From the segmentation of the kidney and the collecting system in 2D or 3D ultrasound images, the system allows to extract an optimal set of morphological (including volumetrics and hydronephrosis index) and appearance descriptors of both structures. These features are used as input parameters of a machine learning algorithm to objectively predict the degree of hydronephrosis of the renal unit. The segmentation of the system can be obtained either by manual or automatic segmentation tools). More specifically, the system is used to identify those cases where further tests would be required. At the same time, the system also identifies hydronephrotic patients where additional tests (including diuretic renography) could be safely avoided. Finally, the system can evaluate surgical patients to assess and potentially predict if surgery provides a significant improvement of the renal function.

First, the embodiments allow the quantitative analysis of the renal units from 2D or 3D ultrasound image data and can be used for the analysis of other organs and objects from similar image data. In particular, the invention relates for the first time ultrasound imaging of the kidneys with renal function. More precisely, the disclosure identifies patients with hydronephrosis that will likely require additional tests and possible surgical intervention, but also patients in which further investigations (such as diuretic renography) could be safely avoided, minimizing the use of ionizing radiation on children while allowing significant savings of human and economic resources. Additionally, the system can assess and potentially predict surgery outcome, identifying those patient whose renal function would improve with surgery.

Key points of this system are listed below: i) It improves the clinical utility of ultrasound imaging for hydronephrosis providing a novel automatic and objective tool as an alternative to traditional and subjective grading system based on simple visual inspection. ii) The system incorporates novel segmentation tools specifically designed to delineate the kidney and the collecting system in 2D and 3D ultrasound images. In particular, these tools provide a detailed analysis of the patient's anatomy (including volumetrics and hydronephrosis index), simulating the evolution of hydronephrosis in the kidney. iii) The system defines a set of optimal appearance features and morphological features of the renal system that allows the establishment of a direct relationship between the shape and appearance of the renal units in ultrasound images and renal functional parameters (e.g. washout time). iv) The system defines new decision boundaries and specific configurations for classifications algorithms that provide maximum sensitivity on identifying severe hydronephrotic cases. v) The system assesses surgical outcome. vi) The system allows the quantification of renal size (and its collecting system). vii) The system permits more objective description and communication regarding the renal unit.

Machine learning and neural networks can also be applied to the algorithms described herein to improve the segmentation and the characterization processes found herein. Moreover, both 2D and 3D images (such as 2D and 3D ultrasound images) can be used as in the medical image input.

The outputs of the segmentation and of the characterization can alternatively be used to perform automatic surgeries or medical interventions. In addition, the output could trigger alarms based on predetermined thresholds. Alternatively, the results can be provided to a physician to assist in diagnosis. Furthermore, the system could provide a suggested diagnosis based on the determination. In addition, the system could assist in a screening process by determining which patients should be further referred for further diagnosis. For instance, the output can objectively describe hydronephrosis and define ultrasound based thresholds of obstruction below which diuretic renography can be safely avoided.

The segmentation algorithms described herein can also be used for other purposes besides medical imaging and processing. For instance, the features described herein could be used to improve the computer and enable quicker and more accurate segmentation for image face detection or any other type of image processing or detection of objects in an image. In addition, many other medical uses can be applied using the claimed algorithms.

Figure 6:
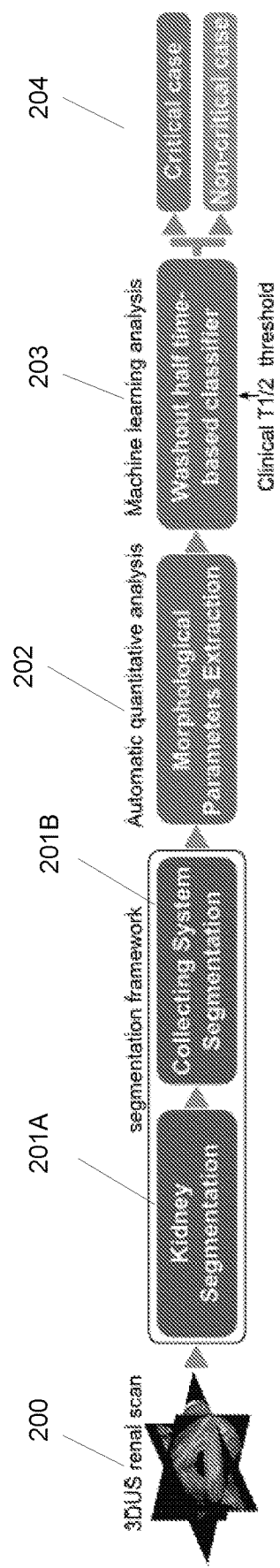
FIG. 6 illustrates a Block diagram showing the principal elements of a system for pediatric hydronephrosis.

An example of the process for characterizing pediatric hydronephrosis is described in FIG. 6. In the example, the input to the system 100 is a 3D ultrasound scan containing the entire volume of the kidney (S200). The segmentation of the kidney (S201A) can be obtained by the automatic segmentation algorithm described above (alternatively by a dedicated interactive segmentation tool with minimal user interaction). The system can apply an automatic kernel convolution-based kidney detector that provides an initial estimation of volume. This initial segmentation may be in an alternative embodiment further refined by defining control points that constrain the deformation of the model. In one embodiment, the system can provide immediate visual feedback, which allows real-time response interactions for fast and accurate kidney segmentation.

Once the kidney has been delineated, the collecting system is segmented (S201B) using an active contour-based formulation designed to replicate the evolution of hydronephrosis in the collecting system of the kidney. Using local phase analysis, the system incorporates a positive delta detector to identify the bands of adipose tissue that surround the collecting system. This allows creating specific probability positional maps to control the propagation of the contour. The detected adipose bands surround the dilated collecting system and constitute a key anatomical clue for its accurate delineation, allowing differentiation from other hypoechoic structures (e.g., renal pyramids). The algorithm is automatically initialized by selecting the darkest 3×3×3 block within the region delimited by the detected adipose tissue.

Steps S201A & S201B may further include framework for the semiautomatic or automatic segmentation and quantification of renal structures (kidney and CS) in 3D ultrasound. The framework is divided in two parts to deal effectively with the particular challenges that arise when working with ultrasound image (for example, with renal images). Described is a kidney segmentation algorithm (S201A) using a Gabor-based fuzzy appearance model (FAM). The segmentation process incorporates shape priors and appearance model tailored to deal with the high intensity variability and inhomogeneity of ultrasound images. Once the kidney is segmented, an active contour-based formulation that mimics the evolution of hydronephrosis within the kidney is used in identifying and segmenting the collecting system (S201B). For instance, a positive delta detector can be used to identify the renal fat in the kidney. On this basis a patient specific stopping function is defined using alpha shapes for the accurate segmentation of the renal collecting system.

In S201A, a weighted statistical shape model can be used to address the contrast dependency with the propagation direction of the ultrasound wave front. Additionally, a weighted fuzzy appearance model (FAM) can be used to deal efficiently with the intensity variability of medical images in general, and ultrasound scans in particular. In the wavefront corrected statistical shape model each kidney, x, is defined as a set of $K \in \mathbb{N}^+$ 3D landmarks distributed across the surface. Using principal component analysis over the aligned training set, $\{x_a\}$, is possible to define a subspace of allowed-shapes by means of the linear equation $y = \bar{x} + P \cdot b$, where $\bar{x}$ is the mean shape, and P is the (3K×t) matrix formed by the $t \in \mathbb{N}^+$ principal eigenvectors required to explain the 98% of the total variance in the training set. Generally, all the landmarks are considered equally relevant when calculating the corresponding shape parameters b of a new instance Y. In particular, $b = P^T(y-\bar{x})$ can be considered as the principal component projection of y that minimizes the squared error function $ERR = \|y - x_a\|^2$. Whereas these expressions provide satisfactory results in most medical applications, in ultrasound imaging it is known that those edges tangent to the propagation direction of the wavefront can be affected by fading effects. These effects hinder the correct localization of the corresponding landmarks, and hence the segmentation process. Suppose W is a (3K×3K) diagonal matrix defining the weight (or reliability) of each landmark. Thus, the error function can be redefined as $ERR_W = (y - x_a)^T W (y - x_a)$, and the corresponding shape parameters, $b_W$, that minimizes it can be obtained as $b_W = [P^T W P]^{-1} P^T W (y - \bar{x})$.

Suppose now that $\vec{d_i}$ is an unitary direction vector that represents the propagation direction of the wavefront at the i-th landmark, $l_i$. Defining the center of the US probe as C, $\vec{d_i}$ can be approximated as $\vec{d_i} \approx \vec{C,l_i}/\|\vec{C,l_i}\|$, where $\|\vec{C,l_i}\|$ represents the Euclidean norm of vector $\vec{C,l_i}$. Therefore, the weight $w_i$ associated with $l_i$ in the shape model can be defined as a function of $\vec{d_i}$, and $\vec{n_i}$, the unitary vector normal to the kidney surface at $l_i$, $$w_i = 1 - \left(\frac{2}{\pi} a\cos \big|_{0,\pi/2} \left(\vec{d_i} \cdot \vec{n_i}\right)\right)^\gamma, \tag{1}$$

where $a\cos|_{0,\pi/2}(\cdot)$ represents the inverse cosine function in the range $[0,\pi/2]$, and $\gamma \in \mathbb{R}$ is a configuration parameter of the power law function. From (1) it can be observed how the weight is 0 for those landmarks where $\vec{d}_i$ and $\vec{n}_i$ are orthonormal, and 1 if parallel.

With regard to the Fuzzy Appearance Model (FAM), while the shape prior model described above ensures the legitimacy of the shapes obtained during the segmentation process, an adequate texture model is another important element. Traditionally, active shape models (ASM) appearance models are based on the normalized first derivative of the gray profiles normal to the boundary of the object and centered at each landmark. Despite the popularity of this simple model, more sophisticated alternatives have emerged over time trying to overcome some of the limitations of the original model. However, all these approaches use a single statistical model to characterize the appearance and texture around each landmark, assuming that there exists a structural consistency among the dataset. While this is just an approximation, differences in the surrounding tissue between patients, depth dependent attenuation in ultrasound images, or inaccuracies in the correspondence between landmarks can lead to noisy or even uninformative appearance models. With regard to an example of the kidney and the liver, typically, the liver is slightly brighter than the kidney. However, the existence of a highly echogenic bands of adipose tissue between both organs or the location of the probe can generate different patterns of appearance. The resulting average profile (μ) is an uninformative intensity pattern. As alternative to the classic single-model approaches, the present disclosure uses multiple appearance models for each landmark in order to capture the inherent differences between datasets, whether they are due to anatomical variability or imaging parameters. A fuzzy clustering theory is used to identify the different appearance patterns of the anatomical region around the landmark $l_i$. Suppose $\{a_{is}\}_{s=1...S}$ represents the training set to model the appearance around $l_i$, where $S \in \mathbb{N}^+$ is the number of training samples. In the most general scenario, $a_{i,s} \in \mathbb{R}^n$ represents the Sth n-dimensional training sample (e.g., a n-dimensional vector containing the intensity profile normal to the contour and centered at $l_i$). Thus, given $\{a_{is}\}_{s=1...S}$, a tailored version of the fuzzy clustering algorithm is used to identify $T_i$ different appearance patterns for each landmark, Each one of these patterns is defined by $\{\mu_{ij}, M_{ij}\}_{j=1,...,T_i}$, where $\mu_{ij} \in \mathbb{R}^n$ and $M_{ij} \in \mathbb{R}^{n \times n}$ represent the mean (center) and the norm-inducing matrix of the j-th cluster respectively. Unlike other fuzzy clustering approaches, $\{\mu_{ij}, M_{ij}\}$ defines the inner-product norm for each cluster, $(a_{i,s}-\mu_{ij})^T M_{ij}(a_{i,s}-\mu_{ij})$ which allows to generate clusters of different geometrical shapes. Note that in the particular case where $T_{i=1}$, $M_i$ and $\mu_i$ represent the sample covariance matrix and the sample mean, respectively, as commonly used in ASM. As discussed above, the contrast, and thus the appearance, around landmark $l_i$ can be significantly affected by the propagation direction of the wavefront at that location. Thus, for each sample, $a_{i,s}$, is possible to define a weight $w_{is}$ (see eq. (1)) that controls the impact of that sample when building the appearance models. The Appendix extends the original fuzzy clustering framework for the more general scenario of a weighted set of samples $\{a_{i,s}, w_{i,s}\}$. The optimal number of clusters, $T_i$, is automatically defined by means of a weighted version of a validation index. In order to increase the robustness of the appearance model against possible inaccuracies in the correspondence between landmarks (i.e., small differences in the anatomical location defined by $l_i$ through the training set), we expand the training set $\{a_{is}\}$ by including the appearance information from adjacent landmarks. In particular, the appearance training set of landmark $l_i$, $\{a_{is}\}$, consists of texture samples extracted from $l_i$ and its neighboring vertices within a ring of length $C'$.

When segmenting a new image using an ASM-based algorithm, the location of each landmark is updated to that position that maximizes the probability of coming from the learned distribution, i.e., minimizing the Mahalanobis distance to the mean profile learned from the training set. Similarly, having now $T_i$ different models, $\{\mu_{ij}, M_{ij}\}_{j=1,...,T_i}$, the optimal location for each landmark will be defined by that model that minimizes the Mahalanobis distance, using the corresponding fuzzy mean and covariance matrix.

Traditional intensity-based appearance models are particularly inefficient when dealing with ultrasound images, due also to the aforementioned inherent challenges, such as speckle and low contrast between areas of interest, among others. The present approach is able to use a Gabor filter-based appearance model, as alternative to the classic intensity-based approaches. Gabor filters can be used in ultrasound image processing for edge detection, texture representation and discrimination, mainly in 2D. A Gabor filter bank can be used to extract and characterize texture features in 3DUS image of the prostate. The present approach can use an omnidirectional Gabor-based appearance model for 3D ultrasound images. A Gabor filter can be expressed mathematically as:

$$g_{f,\theta,\varphi}(x, y, z) = \left(\frac{1}{(2\pi)^{\frac{3}{2}}a^3}\right) e^{-\left(\frac{x^2+y^2+z^2}{2a^2}\right)} \cdot e^{-j2\pi(ux+vy+wz)}, \quad (2)$$

where $u = f \sin\theta \cos\varphi$; $v = f \sin\theta \sin\varphi$; and $w = f \cos\theta$; f is the central frequency of the sinusoidal plane wave, and $\varphi$ and $\theta$ are the orientation parameters that together with the Gaussian scale parameter, $\sigma$, determine the Gabor filter in 3D. The number of filters, and thus the computational cost, increases significantly with the number of orientations, especially in 3D. Typically, only a discrete number of orientations are considered (i.e. $\theta_m = m\pi/M|_{m=0,...,M-1}$ and $\varphi_n = n\pi/N|_{n=0,...,N-1}$), which limits the capacity of the filter to extract texture features in any direction $(\theta, \varphi)$. Suppose $G_{f,\theta_m,\varphi_n}$ represents the filtered 3D ultrasound volume, I, using one of the M·N Gabor filters that sample the entire 3D space. Suppose now the angles $\theta_i$ and $\varphi_i$ represent respectively the zenith and azimuth of the vector $\vec{n}_i$, the unitary vector normal to the kidney at landmark $l_i$. Thus, $G_{f,\theta_i,\varphi_i}$ can be estimated as $$G_{f,\theta_i,\varphi_i} = (1-\eta_i)(1-\beta_i)G_{f,\theta_{mi},\varphi_{ni}} + (1-\eta_i)\beta_i G_{f,\theta_{mi},\varphi_{ni+1}} + \eta_i(1-\beta_i)G_{f,\theta_{mi+1},\varphi_{ni}} + \eta_i\beta_i G_{f,\theta_{mi+1},\varphi_{ni+1}}, \quad (3)$$

where $m_i = \lfloor \theta_i/(\pi/M) \rfloor$, $n_i = \lfloor \varphi_i/(\pi/N) \rfloor$, $\eta_i = (\theta_i/(\pi/M)) - m_i$, and $\beta_i = (\varphi_i/(\pi/N)) - n_i$, $G_{f,\theta_i,\varphi_i}$ are omnidirectional approximations of the discrete filter bank $G_{f,\theta_m,\varphi_n}$ computed for each landmark, $l_i$, during the ASM based iterative segmentation. More specifically, the imaginary component is used to create a new texture model for each landmark. The omnidirectional Gabor filter is able to identify the contour of the kidney in the vicinity of each landmark. Additionally, the multiscale nature of Gabor filter banks allows to characterize textures with different dominant sizes (i.e., using different central frequencies, f), and thus, to improve the robustness of the segmentation method to local minima. Starting with the lowest frequency, the coarse Gabor features are used in the initial stages of the segmentation. As the algorithm evolves, the resulting shape becomes closer to the target, using higher values of f. This framework enables hierarchically focusing on different image features at different stages of the algorithm. Since the texture information is different at each resolution, the fuzzy appearance model is specifically created for each frequency, f. Thus, the Gabor-based fuzzy appearance model for the i-th landmark at frequency f is defined by $\{\mu_{fij}M_{fij}\}_{j=1,\ldots,T_{fi}}$. Algorithm 1 summarizes the key elements of the kidney segmentation method. Typically, most segmentation methods for ultrasound imaging require user interaction to initialize the algorithm, or impose hard positional constraints on the location of the target object. The presently disclosed algorithm requires minimal or no user intervention by selecting point clicks to roughly define when the principal axis of the kidney. These principal axes can be defined as the main axis of the ellipsoid circumscribing the kidney.

ALGORITHM 1
KIDNEY SEGMENTATION ALGORITHM

1. Initialization.
2. Detect the center of the probe, C.
3. for f = $f_{min}$ to $f_{max}$// Multiscale loop.
4.     while (NOT CONVERGENCE) or (MAX ITERATIONS) do
5.         for i = 1 toK// Landmarks updating process.
6.             Calculate normal vector,$\vec{n}_i$.
7.             Calculate $\vec{d}_i = C_iT_i/C_iT_i\|$, and$w_i$using (1).
8.             Calculate $G_{f,\theta_t,\varphi_t}$ using (3).
9.             Extract texture samples.
10.            Update location using $\{\mu_{fij}, M_{fij}\}_{j=1,\ldots,Tfi}$// Using the Mahalanobis distance;
11.        end
12.        Define y by concatenating the updated landmarks and mapping it to the normalized shape space.
13.        Calculate and constraint $b_w$.
14.    Define the new kidney shape.
15. end
16. end In step S201B, a collecting system segmentation example is described. In particular, once the contour of the kidney has been delineated, the segmentation of the collecting system inside the kidney is addressed by the active contour formulation. For instance, the evolution equation described herein incorporates a patient-specific stopping function (SF(·)) using the renal fat as anatomical constraint. The renal fat surrounding the collecting system is automatically detected thanks to a positive delta detector described herein. This fat of the renal sinus is used to define the alpha shape-based patient-specific stopping function that controls the evolution of the segmentation process.

For the active contour formulation there is described an energy function that combines contour and intensity-based terms, and incorporates a new patient-specific positional map as additional stopping criteria. Suppose I:$\Omega \to \mathbb{R}^+$ represents a 3D gray level image in the image domain $\Omega \subset \mathbb{R}^3$, and U:(t,$\Omega$)$\to \mathbb{R}$ is an implicit representation of the collecting system at time t, i.e., the collecting system coincides with the set of points U(t,.)=0. Here the evolution equation of U is defined as $$\frac{\partial U}{\partial t} = SF(I)(\beta \cdot Cont(I, \kappa, c, U) + (1-\beta) \cdot Int(I, U)) \quad (4)$$

where SF(I) represents the new aforementioned stopping function, and $\beta \in [0,1]$ is a constant that balances the contour- and the intensity-based terms, Cont and Int respectively. In particular, $$Cont(I,\kappa,c,U)=g(I)|\nabla U|(\kappa+c)+\nabla c+\nabla g(I)\cdot \nabla U, \quad (5)$$

where $\kappa=div(\nabla U/|\nabla U|)$ is the curvature term computed on the level set of U, c$\in \mathbb{R}^+$ is a constant velocity term, and g(I) is an inverse edge indicator function of the image I.

Typically, g(I) is a gradient-based edge detector, e.g. g(I)=1/(1+|$\nabla \hat{I}$|), where is a smooth version of $\hat{I}$. However, these very simple edge detectors generally perform poorly in ultrasound. Alternatively, we use a local phase-based step function detector, the feature asymmetry (FA) detector. The mathematical formulation of FA, and the resulting edge based stopping function, g(I), are detailed below.

Moreover, a formulation based exclusively on the expansive forces described in (5) would turn inefficient when segmenting objects with weak or missing boundaries. Here, we original gradient-based model is combined with Int(I,U), a minimal intensity variance term, defined as $$Int(I,U)=(\lambda_{out}(I-\mu_{out})^2+\lambda_{in}(I-\mu_{in})^2)|\nabla U|; \quad (6)$$

where $\mu_{out}$ and $\mu_{in}$ are the mean intensities in the exterior and the interior of the collecting system, respectively, $\lambda_{out}$ and $\lambda_{in}$ are two control parameters generally defined as $\lambda_{out}=\lambda_{in}=1$. Intuitively, this new intensity-based term looks for the best separating contour in I, and the optimal expected values $\mu_{out}$ and $\mu_{in}$. Given the hypoechoic nature of the collecting system in ultrasound images (i.e. $\mu_{in} \approx 0$), the second term of Equation (6) prevents the evolution of the contour into brighter areas, whereas the first term acts as expansive force toward dark areas (i.e. toward the collecting system).

With regard to local Phase-Based 3D positive delta detection, there is described a detection approach. In particular, with the evolution of hydronephrosis, part of the renal fat originally located in the renal pelvis is displaced into the kidney, surrounding the dilated collecting system. These bands of fat constitute a key visual clue for the radiologist to differentiate the collecting system from other hypoechoic structures like the renal pyramids. The aim of the new positive delta detector (PDD) described herein is to identify these echogenic regions and to incorporate this anatomical information into the new patient specific stopping function SF(I). To define PDD, local phase analysis of the monogenic signal, a n-dimensional generalization of the Hilbert transform-based analytic representation of 1D signals, is used (also have potential in echocardiography images). Using the Riesz transform, the monogenic signal of a 3D ultrasound image, I, is defined as the 4D vector, $I_M=(I_{BP},I_R)$; where $I_{BP}$ is the resulting image of band-pass filtering I, and $I_R=(I_{Rx}, I_{Ry}, I_{Rz})=I_{BP}*h_x, I_{BP}*h_y, I_{BP}*h_z)$ represents the three Riesz filtered components. The spatial representation of the Riesz filters is defined as $h_k=-k/(2\pi(x^2+y^2+z^2)^{3/2})$, where k represents one of the three coordinates of the 3D ultrasound image, i.e. k=x, y or z. Using an isotropic log-Gabor filter with central frequency $\omega_0$, $g_{LG,\omega_0}$, the monogenic signal can be represented in polar form as $$even_{\omega_0}=g_{LG,\omega_0}*I, \quad (7)$$

$$odd_{\omega_0}=\sqrt{\Sigma_{k=x,y,z}(g_{LG,\omega_0}*I_{Rk})^2}. \quad (8)$$

The local phase can thus be defined as $\Phi_{\omega_0}=a\tan(even_{\omega_0}/odd_{\omega_0})$. The local phase contains structural information of the image, such as the location and orientation of image features, transitions and discontinuities. Typically, these properties are used to detect feature asymmetries in images, e.g., step edges, identifying those points whose absolute value of the local phase is 0 (positive edges), or $\pi$ (negative edges):

$$FA = \sum_\omega \frac{\lfloor |odd_\omega| - |even_\omega| - T_\omega \rfloor}{\sqrt{odd_\omega^2 + even_\omega^2} + \varepsilon}, \quad (9)$$

where $\lfloor \cdot \rfloor$ the operator zeros the negative values, $\varepsilon$ is a small positive constant to prevent division by zero, and $T_\omega$ is a scale specific noise threshold defined as $$T_\omega = \exp(\text{mean}[\log((odd_\omega^2 + even_\omega^2)^{1/2})]) \quad (10)$$

As alternative to the traditional intensity-based approaches, we define the new edge detector in (5) as $g(I)=1-FA$, whose satisfactory performance as edge detector in ultrasound images is appreciated.

Here, local phase properties are also exploited to detect symmetrical image features, positive deltas identified with points whose local phase is close to $+\pi/2$ (i.e. points where $|even_\omega| >> |odd_\omega|$ and $\text{sign}(even_\omega \cdot odd_\omega) > 0$). These points indicate relatively thin echogenic regions (i.e. ridges) inside the kidney, corresponding to fat tissue. Since positive deltas are scale-dependent features, the multi-scale PDD is defined as $$PDD = \sum_\omega \frac{\lfloor \lfloor |even_\omega| - |odd_\omega| - T_\omega \rfloor \cdot \text{sign}(even_\omega \cdot odd_\omega) \rfloor}{\sqrt{odd_\omega^2 + even_\omega^2} + \varepsilon}. \quad (11)$$

It can be observed that $PDD \in [0,1]$ takes values close to 1 near bright bands (i.e., positive delta features), and close to zero otherwise).

Using the fat areas identified inside the kidney, there is created an anatomically justified stopping criteria for the active contour formulation able to prevent the leakage of the contour outside the region delimited by the fat bands. Mathematically, this region can be defined as the interior of the continuous surface circumscribing the fat points located via PDD (i.e., those points where $PDD \approx 1$). In the present case, those points are defined as $PDD_{Th}(I) = PDD \geq 0.8$. However, a densely-sampled point cloud is required by most of the existing point set-based surface reconstruction techniques. That is not the case in most of hydronephrotic kidneys, where the scattered distribution of the inner thin fat results in an unstructured set of dispersed points. Therefore, the use of 3D alpha shapes can be used as an alternative. The concept of alpha shapes is a generalization of the convex hull that formalized the intuitive notion of shape for any random spatial point set data, including non-convex and even non-connected sets of points in 3D. Given a set of points, an alpha shape, $\alpha$, is a family of 3D polyhedrons (i.e. geometrical volume with flat polygonal faces) defined by the configuration parameter $\alpha \in \mathbb{N}^+$. An edge of $S_\alpha$ is defined between two members of the finite set of points if there exists a generalized sphere of radius $1/\alpha$ containing the entire point set and which has the property that the two points lie on its boundary. In particular, $S_0$ represents the convex hull defined by the points.

Given $S_\alpha$ defined by the set of fat points located inside the kidney, the new stopping function $SF(I)$ can be defined as $$SF(I) = 1/1 + \lfloor D(S_\alpha(PDD_{Th}(I)) \rfloor^\tau, \quad (12)$$

where $D(S_\alpha(PDD_{Th}(I)))$ is the signed distance to the alpha shape $S_\alpha(PDD_{Th}(I))$, taking negative or positive values inside and outside the region, respectively; $\tau \in [1, +\infty)$ is a control variable. The value of $SF(I)$ will be 1 inside the alpha shape, and close to zero as we move away from it, thus gradually penalizing the leaking of the contour outside of $S_\alpha(PDD_{Th})$. Note that the computation of PDD (11), and thus SF (12), can be performed offline for the entire image domain $\Omega$.

With regard to the initialization of collecting system segmentation, the initialization of the active contour formulation described above is fully automated by selecting the darkest region within the $S_\alpha$ closest to the uretero-pelvic junction (UPJ) of the kidney. UPJ is an anatomical region that can be automatically identified thanks to the landmark correspondence between cases required to create the statistical shape model of the kidney. Thus, the UPJ can be identified with the position of a predefined landmark in the kidney at the junction between the ureter and the renal pelvis of the kidney.

The automatic initialization process provides a valid seed in most of the cases. A simple interactive process or an automatic process can be used to refine or correct invalid seeds if necessary.

In step S202, the segmented renal structures (i.e., the kidney and the renal collecting system) are automatically processed using image analysis techniques to extract a set of 3D morphological parameters. These parameters can be divided in three different categories: (i) size descriptors, including the relative volume of the collecting system and the kidney, relative surface, and maximum and minimum parenchyma thickness; (ii) geometric shape descriptors, such as the sphericity and the eccentricity of both, kidney and collecting system; and (iii) curvature descriptors, including the average curvature of the kidney, and the curvature dissimilarity between the calices and the kidney. Examples of the morphological descriptors include: Major and minor semi-axis of the kidney, and the maximum and minimum parenchymal thickness. (b) Normalized curvature of the kidney. (c) Normalized curvature of the collecting system. The aim of these parameters is to characterize quantitatively the anatomy of the hydronephrotic renal units, defining potential predictive variables of the functionality of the kidney. From the high dimensional space of predictive variables (e.g. 90 variables), an optimal subset of features is selected by a feature selection framework.

Using a predetermined threshold to define severity (such as T1/2TH min), a support vector machine (SVM) (S203) can be used with radial basis function kernel to classify each case as critical (T1/2>T1/2TH min) or non-critical (T1/2≤T1/2TH min) (S204). Finally, receiver operating characteristic (ROC) curve analysis is used to identify probability thresholds that maximize the sensitivity of detecting severe cases of hydronephrosis; that is, no case with a washout time above the defined threshold is misclassified.

Embodiments of this Disclosure as Described as Follows (1) A method for segmenting an anatomical part, including:
identifying a landmark on a contour/surface of a 2D/3D model of the anatomical part in an ultrasound image;
assigning a weight to the landmark;
identifying different appearance patterns of a region around the landmark based on a previously stored training set; and
applying a filter to the different appearance patterns of the region around the landmark in order to identify contours of the anatomical part.
(2) The method according to (1), wherein the landmark on the contour/surface of the 2D/3D model of the anatomical part is identified by comparing the 2D/3D model of the anatomical part with a plurality of reference models.
(3) The method according to (1)-(2), wherein the weight is assigned to the landmark based on an angle between a propagation direction of an ultrasound wave front and a vector normal with respect to the landmark.
(4) The method according to (1)-(3), wherein a fuzzy clustering algorithm is used to identify the different appearance patterns of the region around the landmark.
(5) The method according to (1)-(4), wherein the training set includes appearance information from adjacent landmarks within a predetermined length from the landmark.
(6) The method according to (1)-(5), wherein the filter characterizes textures of the anatomical part with different dominant sizes.
(7) The method according to (1)-(6), wherein the different appearance patterns are created for a plurality of scales.
(8) The method according to (1)-(7), wherein the anatomical part is a kidney.
(9) A method for segmenting a portion of an anatomical part, including:
identifying echogenic regions of the anatomical part in an ultrasound image to differentiate the portion of the anatomical part from other portions of the anatomical part;
generating, using the identified echogenic regions of the anatomical part, a positional map of the portion of the anatomical part; and
incorporating patient-specific constraints to delimitate the portion of the anatomical part.
(10) The method according to (9), wherein the echogenic regions are identified as fat located inside the portion of the anatomical part.
(11) The method according to (9)-(10), wherein the echogenic regions are identified by exploiting local phase properties of the anatomical part.
(12) The method according to (9)-(11), wherein the echogenic regions result in a natural anatomical constraint, and wherein the echogenic regions circumscribe the portion of the anatomical part.
(13) The method according to (9)-(12), wherein the positional map of the portion of the anatomical part is generated from the identified echogenic regions using alpha shapes.
(14) The method according to (9)-(13), wherein the patient-specific constraints are incorporated using the positional map of the portion of the anatomical part.
(15) The method according to (9)-(14), wherein the anatomical part is segmented by mimicking propagation of fluid inside the anatomical part, using the patient-specific constraints to control a propagation process.
(16) The method according to (9)-(15), wherein the anatomical part is a kidney, and the portion of the anatomical part is a collecting system.
(17) A method for characterizing functionality of an anatomical part to identify severity of a medical condition, the method including:
delineating the anatomical part and segmenting a portion of the anatomical part in ultrasound images;
extracting morphological features of the anatomical part and the portion of the anatomical part using image analysis;
selecting an optimal subset of the morphological features using a supervised or an unsupervised feature selection framework; and
classifying each feature in the optimal subset as critical or non-critical based on a threshold and a classifier, the classifier being one of linear discriminant analysis or a support vector machine.
(18) The method of (17), further including:
grouping the extracted morphological features into a plurality of categories, the plurality of categories including size, geometric shape, curvature, and texture of the anatomical part and the portion of the anatomical part.
(19) The method of (17)-(18), further comprising:
identifying probability thresholds that maximize sensitivity of detecting severe cases of hydronephrosis using receiver operating characteristics (ROC).
(20) The method of claim (17)-(19), wherein the optimal subset is selected using an area under a receiver operating characteristics (ROC) curve.
(21) The method of (18)-(20), wherein the size includes a relative volume of the anatomical part and the portion of the anatomical part, relative area and perimeter of the anatomical part and the portion of the anatomical part, and maximum and minimum parenchyma thickness.
(22) The method of (18)-(20), wherein the geometric shape includes sphericity and eccentricity of the anatomical part and the portion of the anatomical part.
(23) The method of (18)-(21), wherein the curvature includes an average curvature of the anatomical part, and curvature dissimilarity between calices and the anatomical part.
(24) The method of (17)-(23), wherein the threshold is a parameter of a function of the anatomical part, the parameter of the function of the anatomical part including a washout half time of at least one of 20 mins, 30 mins, or 40 mins.
(25) The method of (17)-(24), wherein the anatomical part is a kidney, the portion of the anatomical part is a collecting system, and the medical condition is hydronephrosis.

Having now described embodiments of the disclosed subject matter, it should be apparent to those skilled in the art that the foregoing is merely illustrative and not limiting, having been presented by way of example only. Thus, although particular configurations have been discussed herein, other configurations can also be employed. Numerous modifications and other embodiments (e.g., combinations, rearrangements, etc.) are enabled by the present disclosure and are within the scope of one of ordinary skill in the art and are contemplated as falling within the scope of the disclosed subject matter and any equivalents thereto. Features of the disclosed embodiments can be combined, rearranged, omitted, etc., within the scope of the invention to produce additional embodiments. Furthermore, certain features may sometimes be used to advantage without a corresponding use of other features. Accordingly, Applicant(s) intend(s) to embrace all such alternatives, modifications, equivalents, and variations that are within the spirit and scope of the disclosed subject matter.

The invention claimed is:
1. A method for segmenting an anatomical part, comprising:
identifying a landmark on a contour/surface of a 2D/3D model of the anatomical part in an ultrasound image;
assigning a weight to the landmark;
identifying different appearance patterns of a region around the landmark based on a previously stored training set; and applying a filter to the different appearance patterns of the region around the landmark in order to identify contours of the anatomical part.

2. The method according to claim 1, wherein the landmark on the contour/surface of the 2D/3D model of the anatomical part is identified by comparing the 2D/3D model of the anatomical part with a plurality of reference models.

3. The method according to claim 1, wherein the weight is assigned to the landmark based on an angle between a propagation direction of an ultrasound wave front and a vector normal with respect to the landmark.

4. The method according to claim 1, wherein a fuzzy clustering algorithm is used to identify the different appearance patterns of the region around the landmark.

5. The method according to claim 1, wherein the training set includes appearance information from adjacent landmarks within a predetermined length from the landmark.

6. The method according to claim 1, wherein the filter characterizes textures of the anatomical part with different dominant sizes.

7. The method according to claim 1, wherein the different appearance patterns are created for a plurality of scales.

8. The method according to claim 1, wherein the anatomical part is a kidney.

9. A method for segmenting a portion of an anatomical part, comprising:
   identifying echogenic regions of the anatomical part in an ultrasound image to differentiate the portion of the anatomical part from other portions of the anatomical part;
   generating, using the identified echogenic regions of the anatomical part, a positional map of the portion of the anatomical part; and
   incorporating patient-specific constraints to delimitate the portion of the anatomical part.

10. The method according to claim 9, wherein the echogenic regions are identified as fat located inside the portion of the anatomical part.

11. The method according to claim 9, wherein the echogenic regions are identified by exploiting local phase properties of the anatomical part.

12. The method according to claim 9, wherein the echogenic regions result in a natural anatomical constraint, and wherein the echogenic regions circumscribe the portion of the anatomical part.

13. The method according to claim 9, wherein the positional map of the portion of the anatomical part is generated from the identified echogenic regions using alpha shapes.

14. The method according to claim 9, wherein the patient-specific constraints are incorporated using the positional map of the portion of the anatomical part.

15. The method according to claim 9, wherein the anatomical part is segmented by mimicking propagation of fluid inside the anatomical part, using the patient-specific constraints to control a propagation process.

16. The method according to claim 9, wherein the anatomical part is a kidney, and the portion of the anatomical part is a collecting system.

17. A method for characterizing functionality of an anatomical part to identify severity of a medical condition, the method comprising:
   delineating the anatomical part and segmenting a portion of the anatomical part in ultrasound images;
   extracting morphological features of the anatomical part and the portion of the anatomical part using image analysis;
   selecting an optimal subset of the morphological features using a supervised or an unsupervised feature selection framework; and
   classifying each feature in the optimal subset as critical or non-critical based on a threshold and a classifier, the classifier being one of linear discriminant analysis or a support vector machine.

18. The method of claim 17, further comprising:
   grouping the extracted morphological features into a plurality of categories, the plurality of categories including size, geometric shape, curvature, and texture of the anatomical part and the portion of the anatomical part.

19. The method of claim 17, further comprising:
   identifying probability thresholds that maximize sensitivity of detecting severe cases of hydronephrosis using receiver operating characteristics (ROC).

20. The method of claim 17, wherein the optimal subset is selected using an area under a receiver operating characteristics (ROC) curve.

21. The method of claim 18, wherein the size includes a relative volume of the anatomical part and the portion of the anatomical part, relative area and perimeter of the anatomical part and the portion of the anatomical part, and maximum and minimum parenchyma thickness.

22. The method of claim 18, wherein the geometric shape includes sphericity and eccentricity of the anatomical part and the portion of the anatomical part.

23. The method of claim 18, wherein the curvature includes an average curvature of the anatomical part, and curvature dissimilarity between calices and the anatomical part.

24. The method of claim 17, wherein the threshold is a parameter of a function of the anatomical part, the parameter of the function of the anatomical part including a washout half time of at least one of 20 mins, 30 mins, or 40 mins.

25. The method of claim 17, wherein the anatomical part is a kidney, the portion of the anatomical part is a collecting system, and the medical condition is hydronephrosis.

26. The method of claim 17, further comprising:
   identifying the severity of the medical condition based on classifying each feature in the optimal subset as critical or non-critical.

* * * * *